United States Patent [19]
Singh-Derewa et al.

[11] Patent Number: 5,803,923
[45] Date of Patent: Sep. 8, 1998

[54] PRESBYOPIA CORRECTION USING A PROTECTED SPACE PATTERN, METHODS AND APPARATUS

[75] Inventors: Jugvir Inder Singh-Derewa, Orlando, Fla.; Heraldo Sa Martins; Etelvino Teixeira Coelho, both of Madalena Recife, Peru

[73] Assignee: Jugvir I. Singh-Derewa, Darien, Conn.

[21] Appl. No.: 306,660

[22] Filed: Sep. 15, 1994

[51] Int. Cl.$^6$ .................................................. A61N 5/02
[52] U.S. Cl. .................................................. 606/5; 606/4
[58] Field of Search ..................... 606/4, 5, 13; 128/745

[56] References Cited

U.S. PATENT DOCUMENTS

| | | | |
|---|---|---|---|
| 4,798,204 | 1/1989 | L'Esperance, Jr. | 606/5 |
| 4,840,175 | 6/1989 | Peyman | 606/5 |
| 5,102,409 | 4/1992 | Balgorod | 606/5 |
| 5,196,027 | 3/1993 | Thompson, Jr. | 606/5 X |
| 5,318,047 | 6/1994 | Davenport et al. | 606/5 X |
| 5,376,086 | 12/1994 | Khoobehi et al. | 606/4 |

FOREIGN PATENT DOCUMENTS

94/09849  5/1994  WIPO ..................................... 606/4

Primary Examiner—Sam Rimell

[57] ABSTRACT

A zone of increased curvature is produced in the inferior lower quadrants of the cornea FIG. 1 (5). This zone produces a "plus effect" FIG. 2 (5) which leads presbyopia patients to be able to read from near distance again. Such effect is achieved using photoablitive techniques and fixation, patterns, and apparatus specially designed.

2 Claims, 11 Drawing Sheets

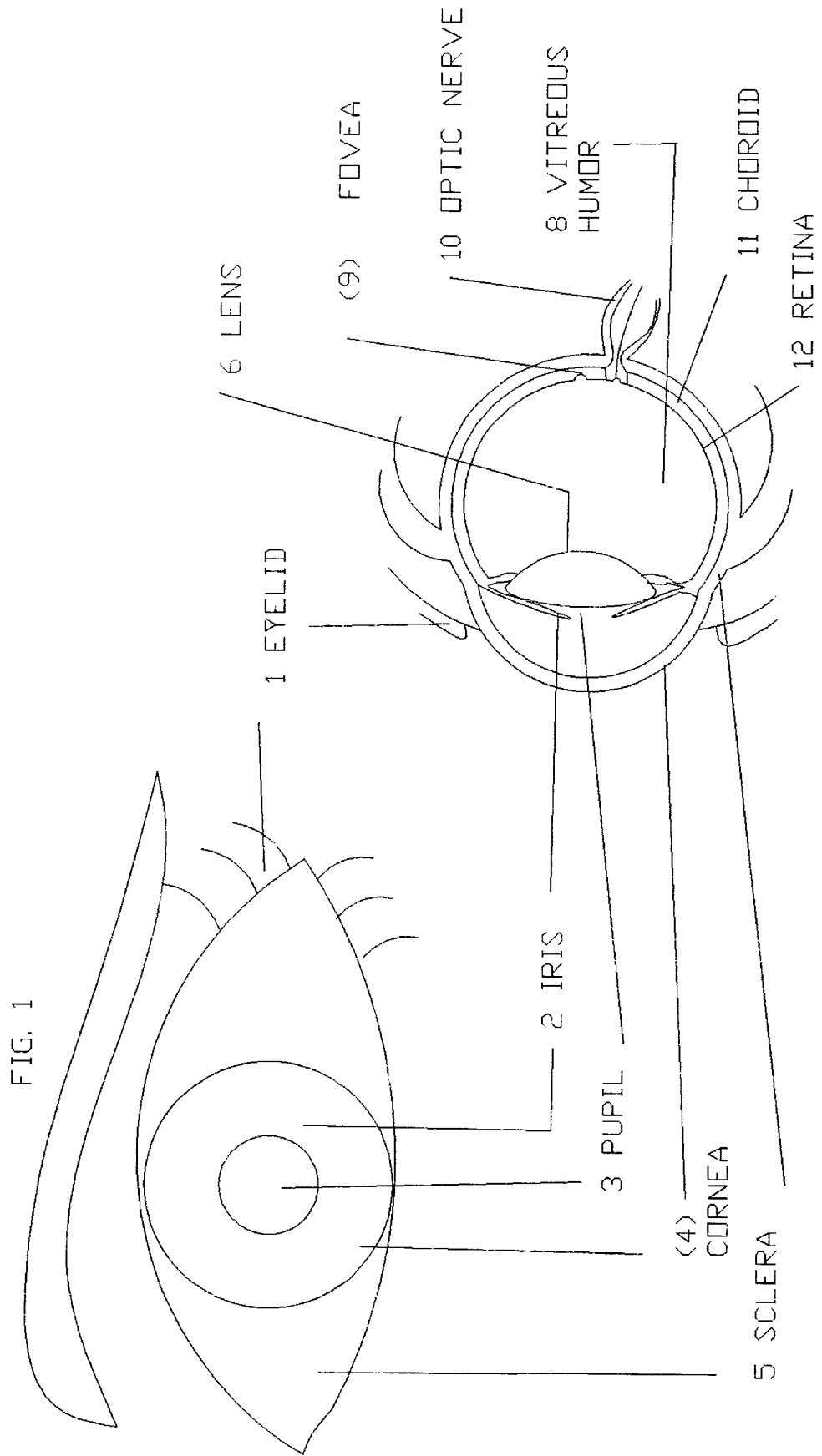

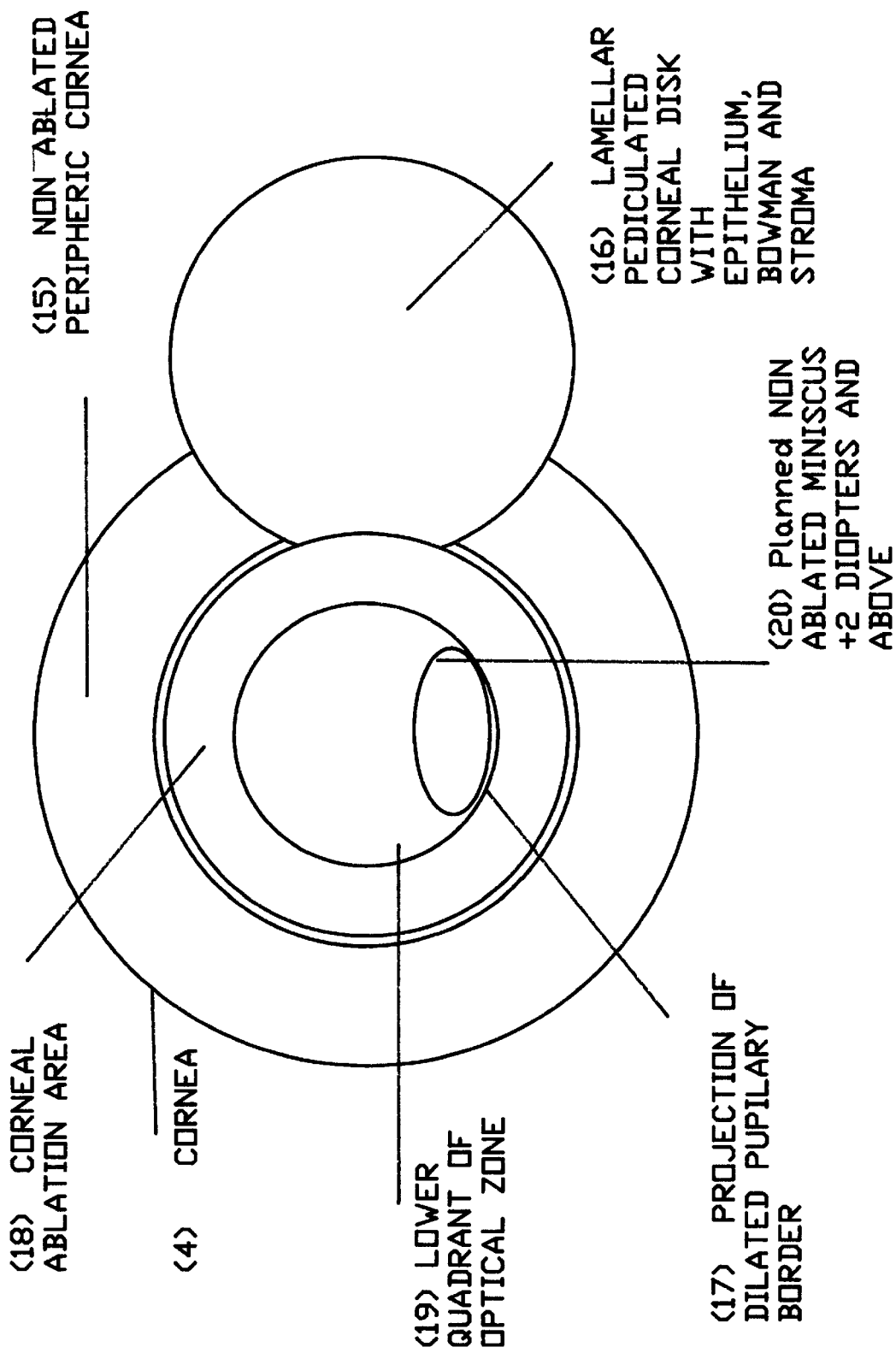

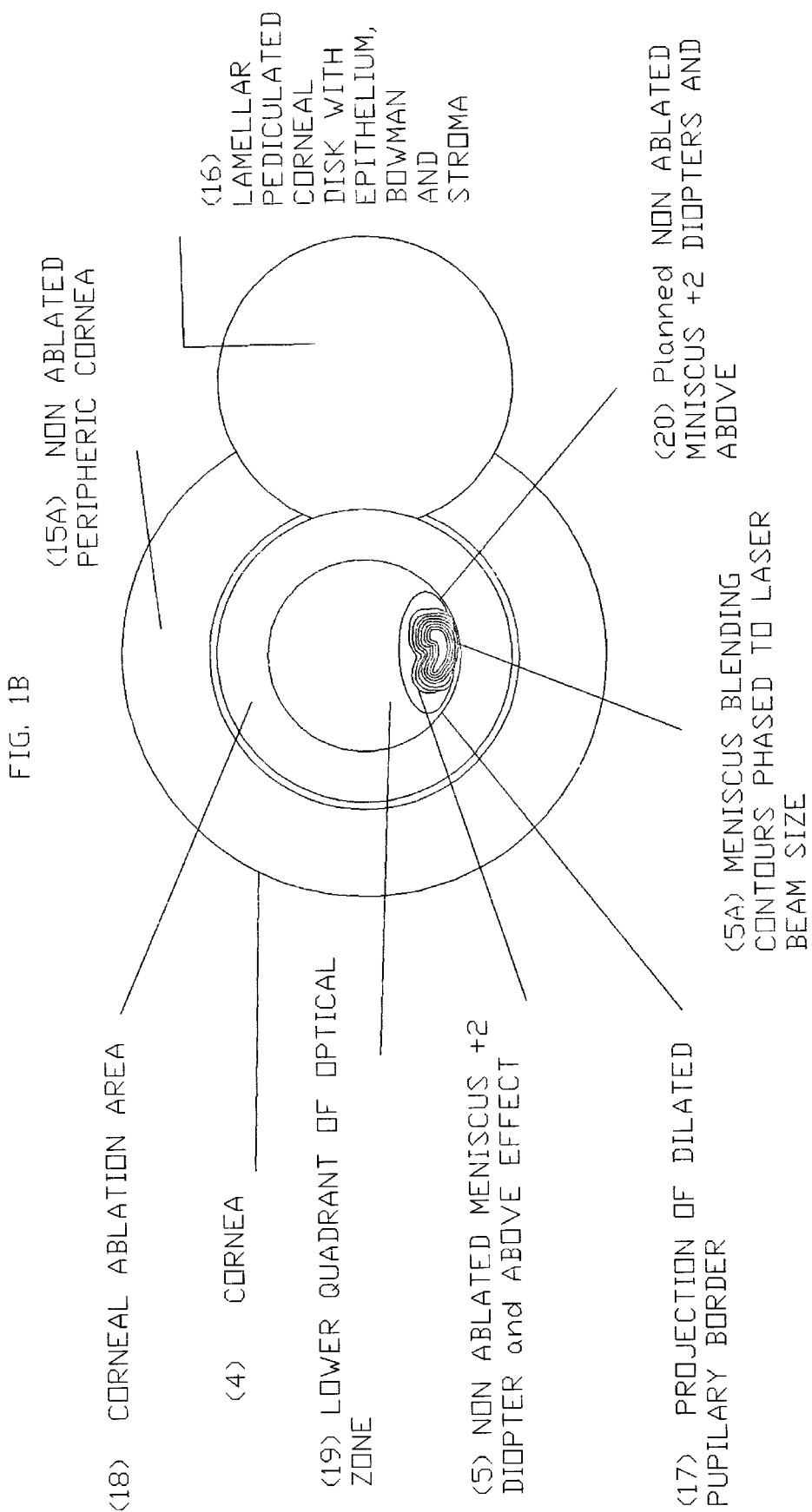

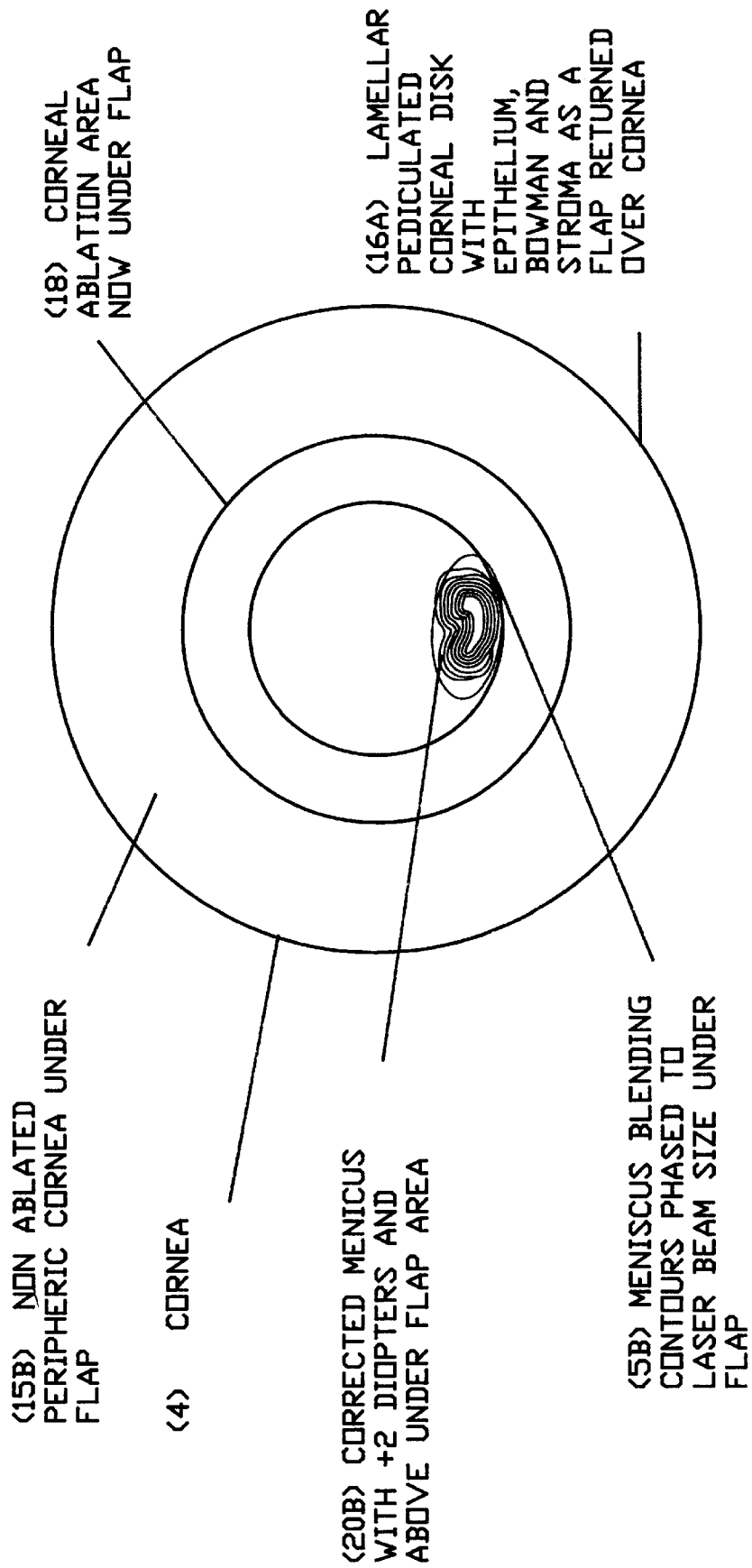

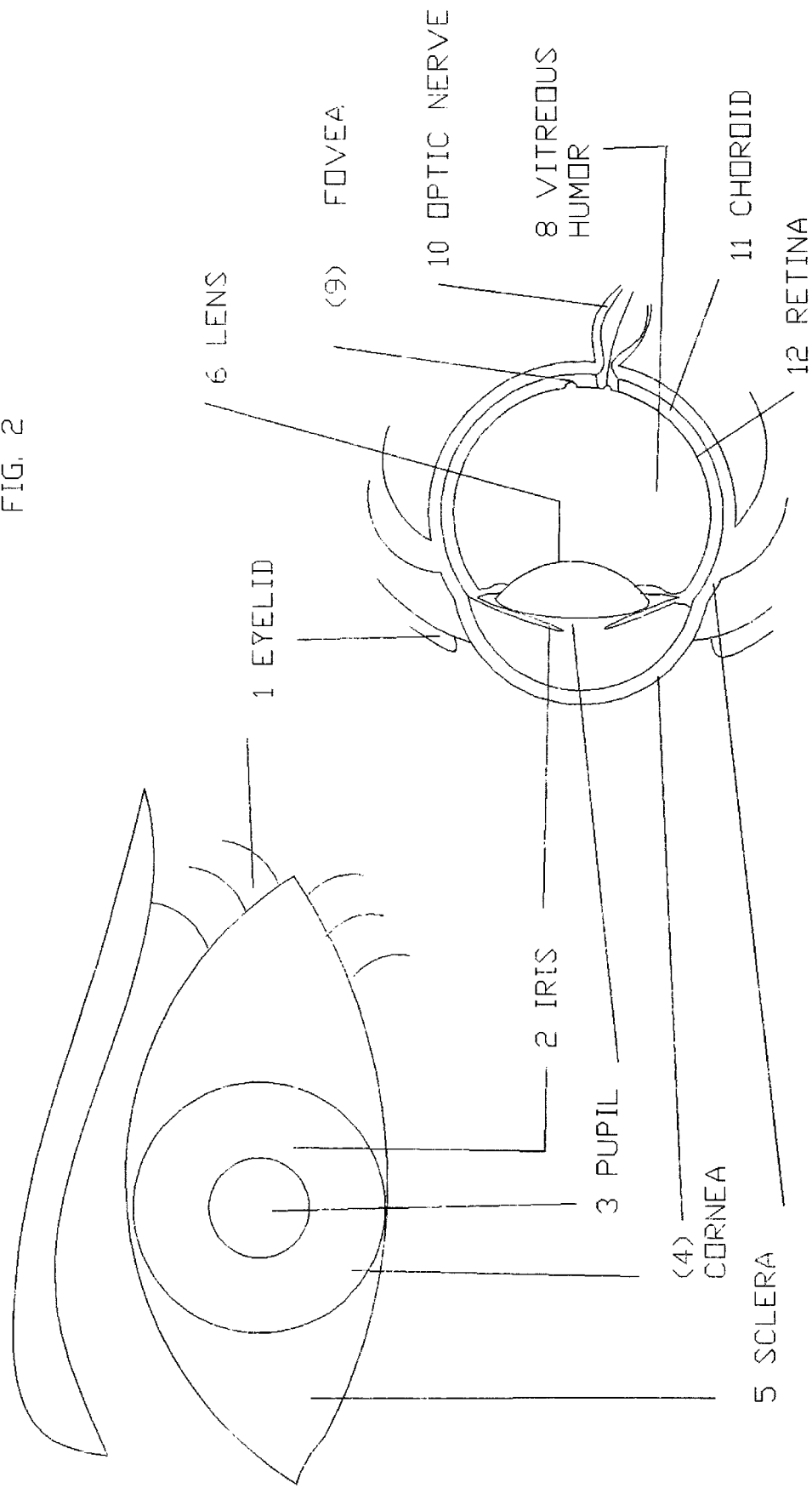

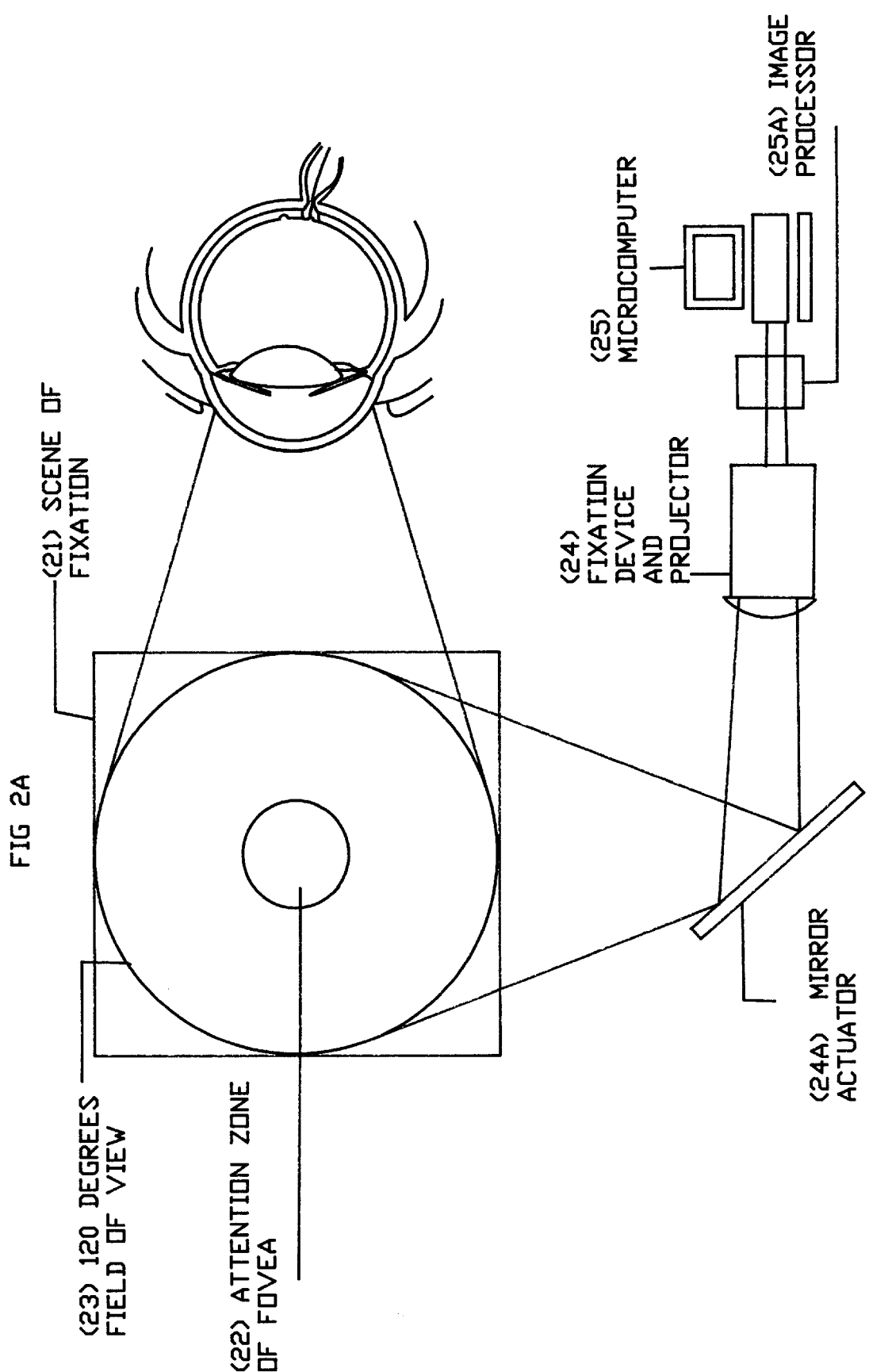

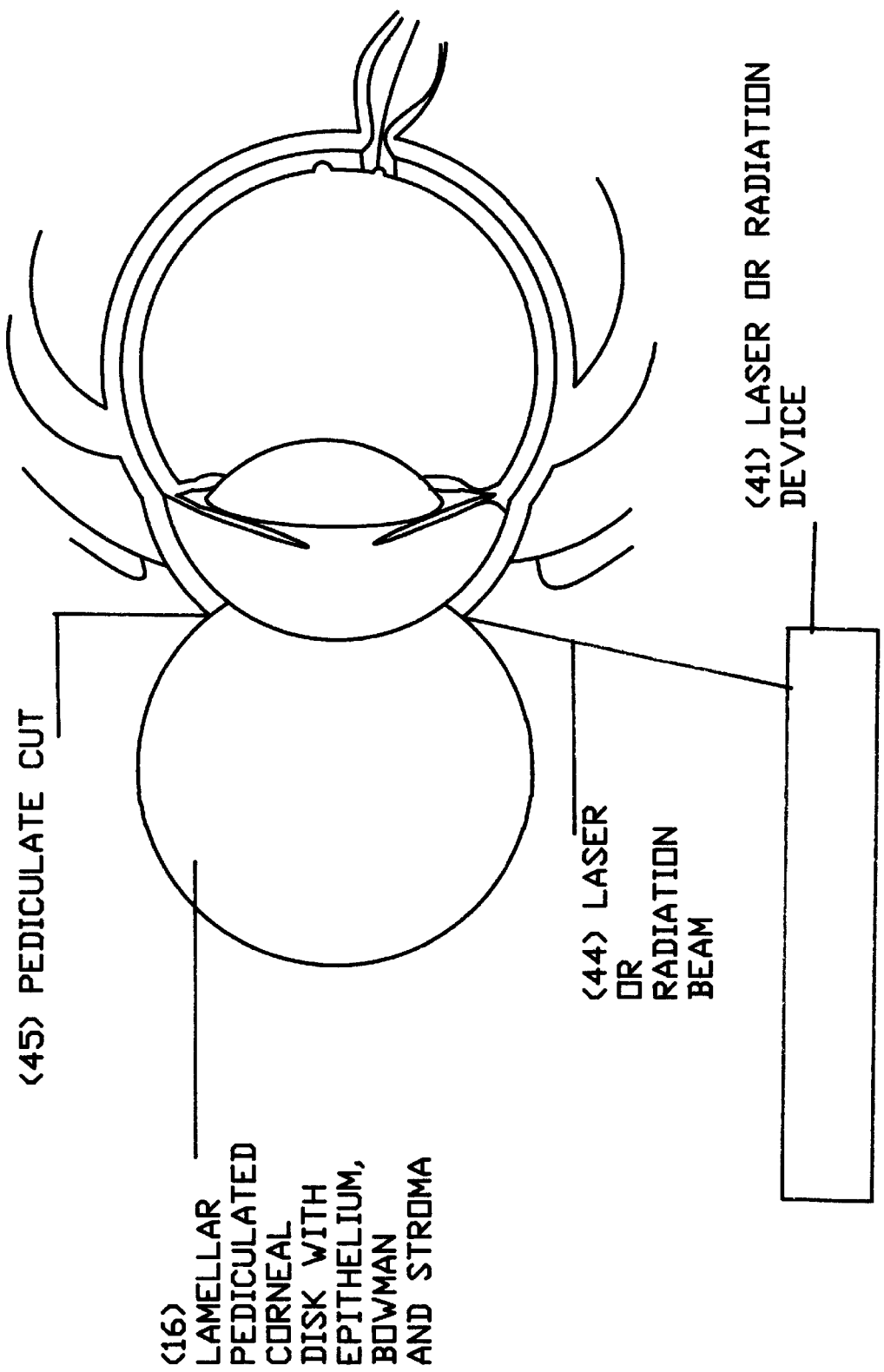

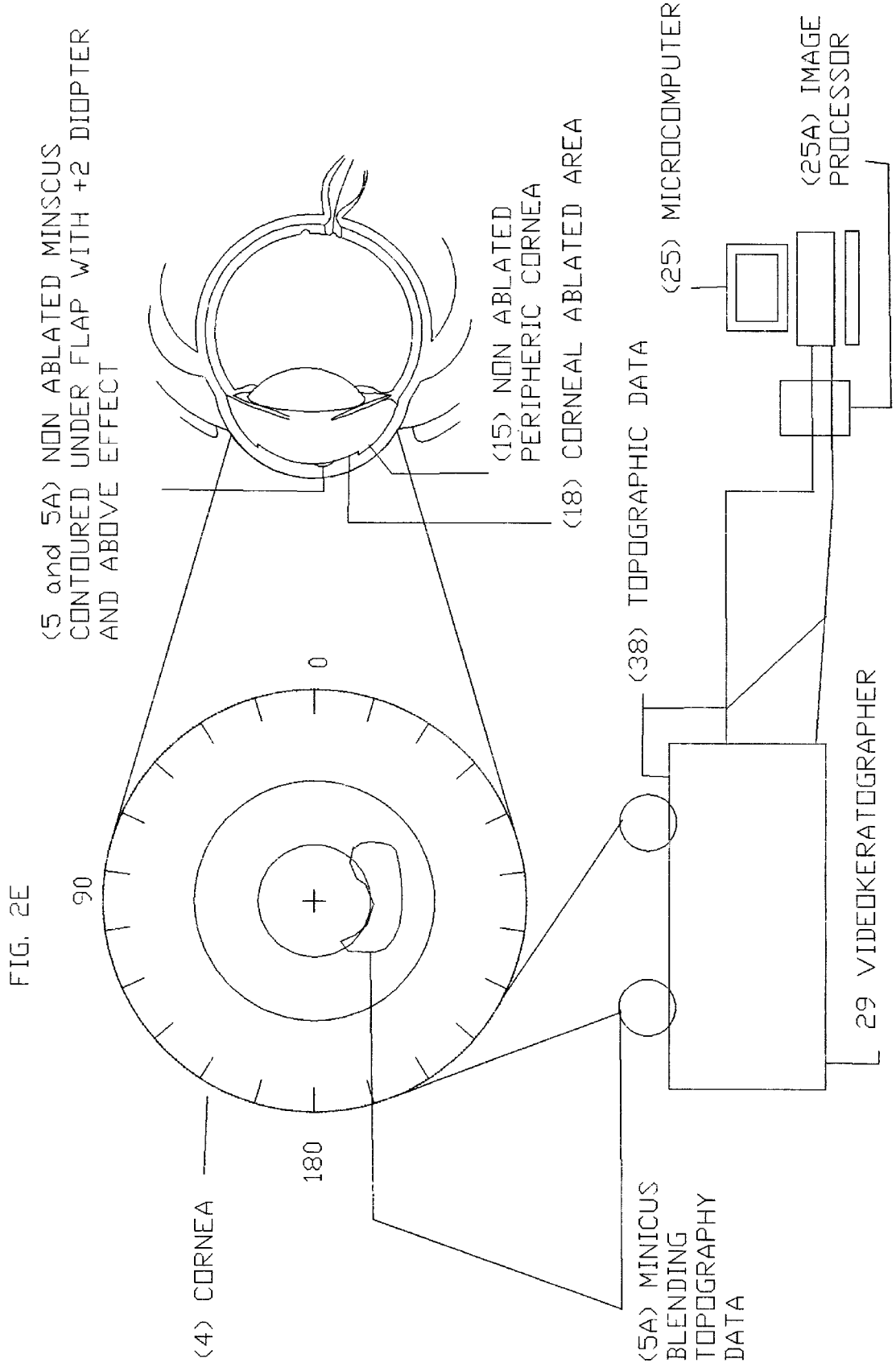

PRESBYOPIA CORRECTION USING A PROTECTED SPACE PATTERN, METHODS AND APPARATUS

CROSS REFERENCE TO RELATED APPLICATIONS

BACKGROUND—FIELD OF INVENTION

THIS INVENTION CONCERNS THE CORRECTION OF PRESBYOPIA. This invention uses a "protected bean/kidney shaped space" in the lower quadrants of the central optical zone of the cornea, nasally oriented. The nasal orientation is optional. This "protected bean/kidney shaped space" in the lower quadrants of the central optical zone of the cornea produces a localized increase in corneal curvature, producing the correction of Presbyopia.

Accurate results in the correction of Presbyopia is achieved by using masks, fixation devices, markings and projections and "protected bean/kidney shaped space" ablation software and hardware to produce such a pattern using ablation ray techniques to change the shape of the cornea.

BACKGROUND—DESCRIPTION OF PRIOR ART

1. Field of Invention

The invention creates a change in the shape of the Cornea of eye. The procedure is to create a "protected bean/kidney shaped space" in a specified region of the cornea, below the epithelium. An ablation methods, on the exposed surface of the cornea, below the epithelium, alters the topography of the cornea and produces the correction for Presbyopia.

2. Discussion of Prior Art

The purpose of the protection of specifically shaped space, while modifying the rest of the cornea to change the shape of the cornea, is to correct for presbyopia. But accurately correcting the dimensional and optical characteristics of the cornea and its radius of curvature in the manner specified in the invention. There is no prior art.

Unsuccessful attempts have been made to correct presbyopia by cornea sculpting either circular, annular, or multiconcentric areas.

OBJECTS AND ADVANTAGES

The object of the invention is to change the shape of the cornea to correct Presbyopia by creating a special "protected bean/kidney shaped space" protected area in the lower quadrant of the optical zone. The "protected bean/kidney shaped space" occupy an average of 30% of the useful central optical zone and its borders have a slight transition from the "emetropic cornea" to the "plus effect" cornea.

OTHER OBJECTS AND ADVANTAGES

1. Lamellar-Excimer or Solid State Laser or mask technique

The method delineates a thin lamellar disk a Lamellar Pediculated corneal disk with Corneal Epithelium, Bowman's Membrane and Stroma (consisting of multiple layers of collagen fibers, kerotocytes and water usually about 120 microns to 160 microns thick made by the use of microkerotome of laser with total diameter of 7.5. m.m. This disk is preserved and returned to promote healing.

2. Stromal ablation is carried in a diameter large enough not to change the primary emmetropic status of the eye, or with variations in the diameter, depth and direction for correcting primary pre existing ametropiares but leaving the "protected bean/kidney shaped space" in the lower quadrants of the central optical zone, with a height and width compatible with the generation of a +2 diopter and up effect.

3. The "protected bean/kidney shaped space" which is an elevated area and the "plus effect" use computational methods and laser control is used to create the accurate "Bean/Kidney shaped area") with resulting correction of presbyopia "Bean/Kidney shaped area" is placed and contoured in the lower quadrant of the central optical zone and new relationship between the slope angle created by the Meniscus blending contours phased to laser beam size to blend into surface corneal ablated area. Proper centration the centration, pupil placement magnification and other surgeon's magnification and alignment instrument by tracking mechanism or immobilization or indenting marks, Projection of Dilated Pupilary Border the surgeon aligns the cornea) and centers the cornea along the optical axis of the eye and "Bean/Kidney shaped area" is planned then placed and contoured in the lower quadrant of the central optical zone.

4. Direct Corneal Ablation is a another option to place "protected bean/kidney shaped space" by not using the lamellar disc and to start the ablation directly on the epithelium or the Bowman's Membrane.

5. A slight decentration of "protected bean/kidney shaped space" in the direction of nasal direction has been incorporated into the orientation of the invention. The orientation is optional and recommended.

6. In transepithelial ablation the beveled shaped mask edges will provide for smother transition as will contoured laser topographical blending.

7. The correction of presbyopia, using the method of this invention is far superior to the using intra ocular lenses since does not have the drawback and problems associated with decentration. The invention makes it possible to correct for reading distance and is the optimal method of correction for the patient.

8. The software and hardware in programmed to create "protected bean/kidney shaped space" and the ablation of the tissue to produce to the correct expected result so the efficiency of the method and technique is optimized for the correction of presbyopia.

9. The technique avoids the correction of presbyopia using circular or multi concentrical zone methods. Circular and multiconcentric methods produce many symptoms, such as glare, decrease in contrast sensitivity and monocular dyplopia among others.

Still further objects and advantages will become apparent from a consideration of the ensuing drawings and description.

BRIEF DESCRIPTION OF THE DRAWINGS

FIG. 1 Shows the front of the eye and the cornea (4) is the clear fibrous tissue forming the front surface of the eye. Other eye components, not all, responsible for feeding accurate visual information are labeled.

FIG. 1A Identifies the transparent front cover responsible for about 60% of the refracting power of the eye, the cornea (4), a Lamellar Pediculated corneal disk with Corneal Epithelium (approx. 40–50 microns thick), Bowman's Membrane and Stroma (consisting of multiple layers of collagen fibers, kerotocytes and water) (16), a planned NON Ablated Miniscus +2 and above (20) projection marking, a Projection of Dilated Pupilary Border (17), the region in the Lower Quadrant of Optical Zone (19) an exposed Corneal Ablation Area (18) and the area of Non-Ablated Peripheric Cornea (15).

FIG. 1B identifies cornea (4) and the changes in corneal topography. The corneal surface has a non-ablated peripheric cornea (15A), a changed curvature of the surface in the corneal ablation area (18), a new changed slope and curvature as a result of the non ablated meniscus +2 Diopter and above effect (5) in the lower quadrant of the optical zone (19) and new relationship between the slope angle created by the Meniscus blending contours phased to laser beam size to blend into surface corneal ablated area (18). Identified are a projection of Dilated Pupilary Border (17) the planned Non-Ablated Meniscus +2 Diopters and above area and the delineated, but attached Lamellar Pediculated disk with epithelium, Bowman and Stroma (16) preserved for replacement.

FIG. 1D Shows the eye corrected for presbyopia and the accurate changed shape of the cornea to determined visual acuity. The optical, anatomical, and physiological data are shown as the non-ablated peripheric cornea (15B) returned under the flap, a corrected meniscus with +2 diopter and above correction under the flap, the (5B) meniscus blending contours phased to a laser beam size under the flap and the Corneal Ablation area now under the flap (18). The flap being (16A) the Lamellar Pediculated Corneal Disk with Epithelium, Bowman and Stroma is returned over the cornea to complete the correction for presbyopia.

FIG. 2 Shows a lateral cross-section of the human eye while in contact with air and feeding visual information to the brain. The transparent front cover responsible for about 60% refractive power of the eye, the cornea (4) bends most of the light rays, the lens (6) also bends the light to insure that a sharp image is focused on the retina 12.

FIG. 2A Identifies the Attention Zone of the Fovea (22) within a 120 Degrees Field of View (23). A scene of fixation (21) to fixate the eye is projected by a fixation device and projector (24) with a scanning actuated mirror (24A) and the data is feed into the image processor (25A) and Microcomputer (25).

FIG. 2D Is the preferred creation of the Lamellar Pediculated Corneal disk with Epithelium, Bowman and Stroma (16), where the Pediculate Cut (45) is made using a laser (41) and laser beam (44) rather than a microkeratome. The Lamellar Pediculated Corneal disk with Epithelium, Bowman and Stroma (16), is then seperated and positioned as shown in the figure, as a flap.

FIG. 2E Identifies a videokerotograph 29, which is a device used to extract shape information from the patient's cornea, which passes Topographic data from the Cornea (4) and Miniscus Blending Topographic Data (5A) to the microcomputer (25) and image processor (25A). (5 and 5A) Non-Ablated Miniscus Contoured under Flap with +2 Diopter and above effect is shown as a lateral cross-section indicating the new curvature, (18) is the Corneal Ablated Area and (15) is the Non-Ablated Peripheric Cornea.

SUMMARY

Preferred Embodiment—Description

Figure 1C:
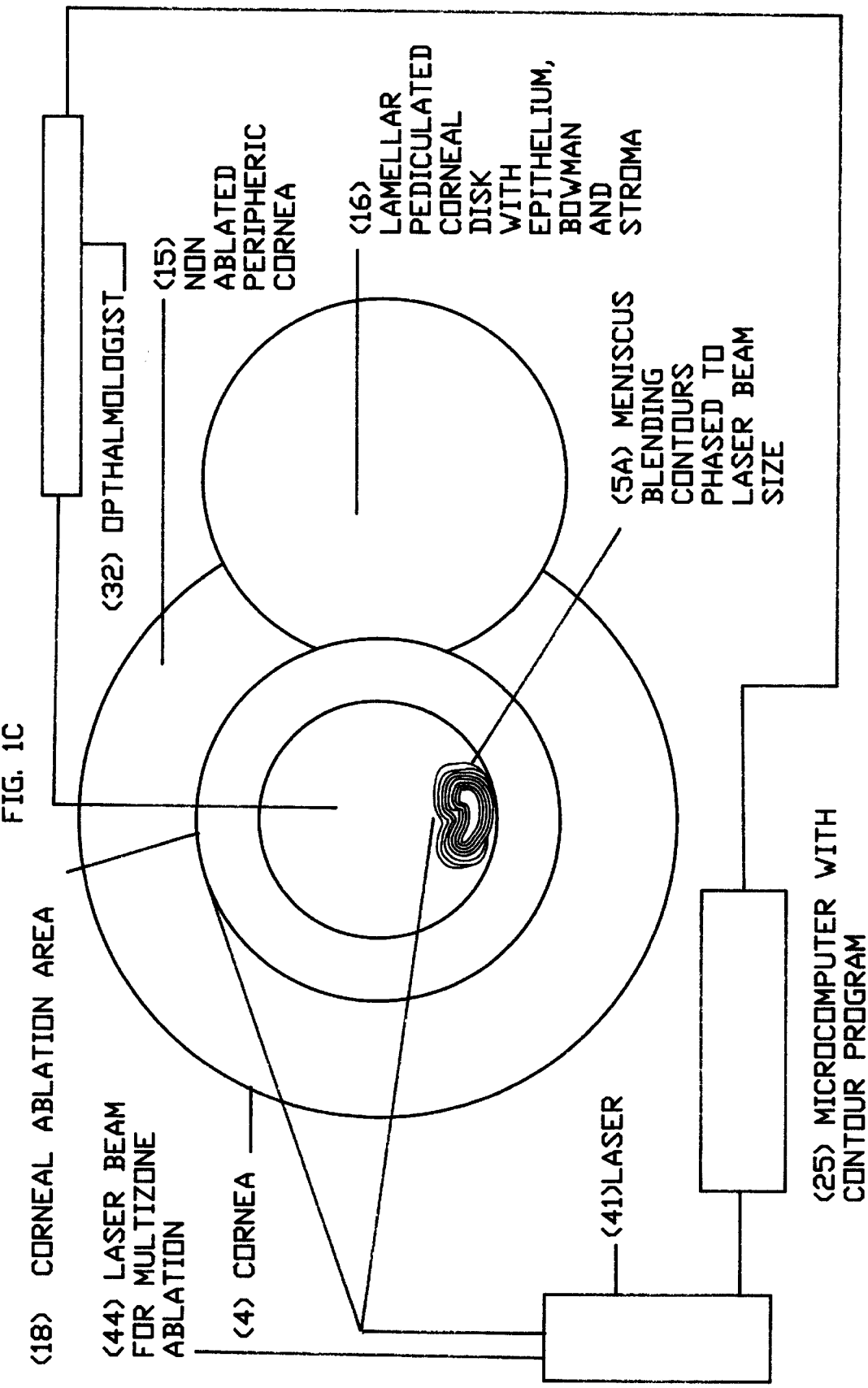
FIG. 1C Identifies the methods and instruments used allowing the ophthalmologist to direct shape information and laser beam for multizone ablation (44) to the patients cornea (4). The laser (41) beam (44) are directed to ablate the surface of the Corneal Ablation Area (18), create a changed curvature of the surface in the corneal ablation area (18), a new changed slope and curvature as a result of the non ablated meniscus +2 Diopter and above effect (5) in the lower quadrant of the optical zone (19) and new relationship between the slope angle created by the Meniscus blending contours phased to laser beam size to blend into the surface of the corneal ablated area (18). Identified are predetermined Meniscus blending contours phased to the beam size (5A). Identified are the interactive control paths carrying bidirectional information from the patients cornea (4) to the ophthalmologist (32), the centration and ablation management (31), computer (25), and laser (41) and laser beam for multizone ablation (44). Also identified is the preserved Lamellar Pediculated disk with epithelium, Bowman and Stroma (16).

The shape of the cornea, a clear, fibrous tissue forming the front of the surface of the eye is very important in determining visual acuity and a description of the operation to correct presbyopia by protecting a "Bean/Kidney shaped area" (5 & 5A) while modifying the remaining dimensional optical characteristics of the cornea are illustrated in FIGS. 1–1D and FIGS. 2–2E.

FIG. 1 Shows the front of the eye and the cornea (4) is the clear fibrous tissue forming the front surface of the eye. Other eye components, not all, responsible for feeding accurate visual information to the brain are labeled.

FIG. 2 Shows a lateral cross-section of the human eye while in contact with air and feeding visual information to the brain. The transparent front cover responsible for about 60% refractive power of the eye, the cornea (4) bends most of the light rays, the lens (6) also bends the light to insure that a sharp image is focused on the retina 12.

FIG. 2A Identifies patient's self fixating attention Zone of the Fovea (22) within a 120 Degrees Field of View (23). A scene of fixation (21) to fixate the eye is projected by a fixation device and projector (24) with a scanning actuated mirror (24A) and the data is supplied into the image processor (25A) and Microcomputer (25) and the data from fixation scene is fed to alignment instruments through the surgeon's microscope.

Figure 2B:
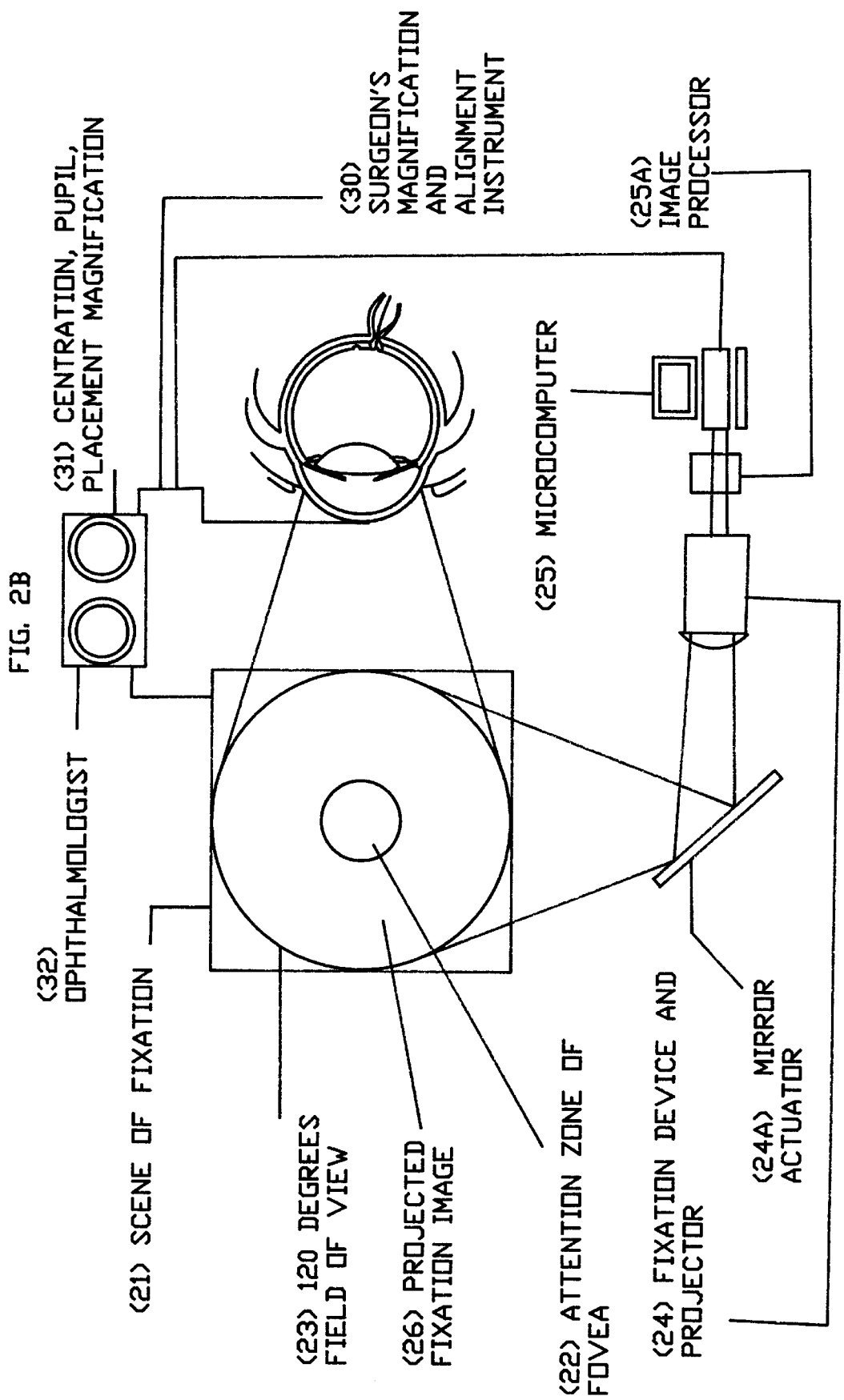
FIG. 2B Illustrates relationships and measure of corneal topography, the shape of the corneal surface from an array of discrete measure to provide an expression of corneal shape and presbyopia shape correction which data is streamed into the microcomputer (25) and image processor (25A) The ophthalmologist (32) also using centration, pupil placement magnification (31) and other surgeon's magnification and alignment instrument (30) projects a scene of fixation (21) and the projected fixation image (26) encompasses 120 degrees field of view (23) and is centered on the Attention Zone of Fovea (22) and the data is controlled on the feed forward and backward loop by the scanning mirror actuator (24A) the fixation device and projector, the image processor and interactively through the microcomputer back to the ophthalmologist (32).

FIG. 2B Illustrates relationships and measure of corneal topography, the shape of the corneal surface from an array of discrete measure to provide an expression of corneal shape and presbyopia shape correction which data is streamed into the microcomputer (25) and image processor (25A) The ophthalmologist (32) also using centration, pupil placement magnification (31) and other surgeon's magnification and alignment instrument (30) projects a scene of fixation (21) and the projected fixation image (26) encompasses 120 degrees field of view (23) and is centered on the Attention Zone of Fovea (22) and the data is controlled on the feed forward and backward loop by the scanning mirror actuator (24A) the fixation device and projector, the image processor and interactively through the microcomputer back to the ophthalmologist (32). This data which represents the subtle shape characteristics about the cornea is used to calibrate values to arrive at the shape of the eye to correct for presbyopia.

Figure 2C:
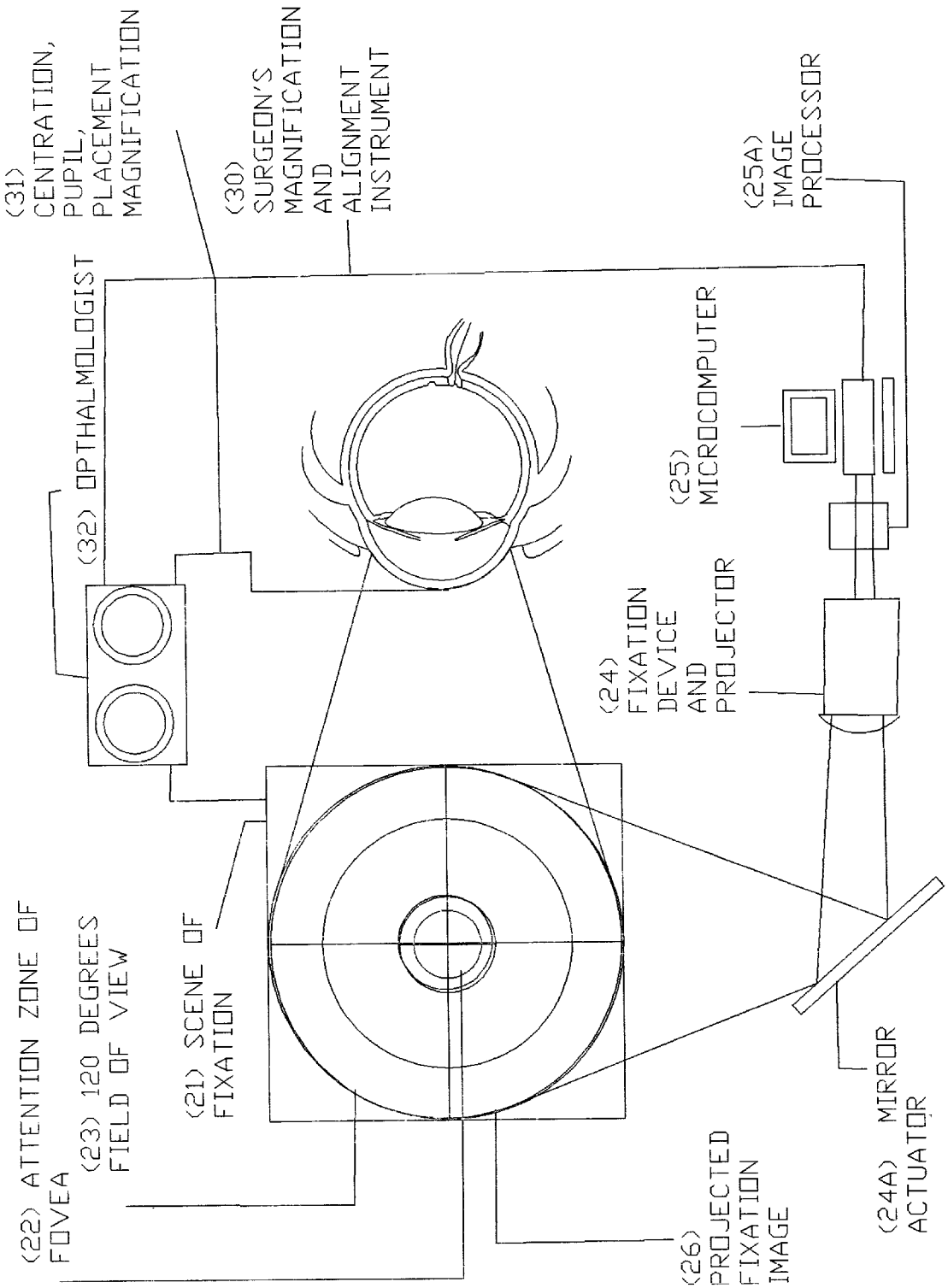
FIG. 2C identifies the relationship of the ophthalmologist (32) and patients cornea to develop the data axial and instantaneous power. centration, pupil placement magnification data control to microcomputer (25), the surgeon's magnification and alignment (30) for corneal topography data and control to the microcomputer (25). Patients data from the Attention zone of Fovea (22), encompassing 120 Degrees Field of View (23) is acquired from within the Scene of Fixation (21) projected onto the cornea by the projected fixation image (26). Identified are the fixation device and projector (24) and mirror actuator (24A) and image processor (25A).

FIG. 2C identifies the relationship of the ophthalmologist (32) and patients cornea to develop the data axial and instantaneous power. centration, pupil placement magnification data control to microcomputer (25), the surgeon's magnification and alignment (30) for corneal topography data and control to the microcomputer (25). Patients data from the Attention zone of Fovea (22), encompassing 120 Degrees Field of View (23) is acquired from within the Scene of Fixation (21) projected onto the cornea by the projected fixation image (26). Identified are the fixation device and projector (24) and mirror actuator (24A) and image processor (25A). The computational methods are used to measure the "Bean/Kidney shaped area" (5 & 5A) which may appear as slight distortion in cornea and is small compared to relative overall shape.

FIG. 1A Identifies the transparent front cover responsible for about 60% of the refracting power of the eye, the cornea (4) whose shape is to be changed. A Lamellar Pediculated corneal disk with Corneal Epithelium (approx. 40–50 microns thick), Bowman's Membrane and Stroma (consisting of multiple layers of collagen fibers, kerotocytes and water) (16) which has been delineated, mechanically using a dulled Beaver Blade or by laser and left attached and preserved for replacement is seen. A planned NON Ablated Miniscus +2 and above (20) projection marking is made either mechanically or referenced by projection is then created on the exposed Corneal bed, a Projection of Dilated Pupilary Border (17) is also made either mechanically or by projection, an exposed Corneal Ablation Area (18), which is Descemet's membrane, a membrane that is located beneath the stroma and above the endothelial cell layer, and the area of Non-Ablated Peripheric Cornea (15) is seen.

FIG. 1B Light is refracted when it passes between mediums with differing refractive indices, of the eye (tear layer, cornea, lens, etc.) the biggest difference is between the cornea and the air, thus the shape of cornea has the most influence on the quality of vision and by using accurate shape information presbyopia vision problems are corrected. The Figure identifies cornea (4) and the changes in corneal topography. The corneal surface has a non-ablated peripheric cornea (15A), a changed curvature of the surface in the corneal ablation area (18), a new changed slope and curvature as a result of the non ablated meniscus +2 Diopter and above effect (5) in the lower quadrant of the optical zone (19) and new relationship between the slope angle created by the Meniscus blending contours phased to laser beam size to blend into surface corneal ablated area (18). Identified are a projection of Dilated Pupilary Border (17) the planned Non-Ablated Meniscus +2 Diopters and above area and the delineated, but attached Lamellar Pediculated disk with epithelium, Bowman and Stroma (16) preserved for replacement. The operation is the result of determining corneal shape measurements and the placement of "Bean/Kidney shaped area" (5& 5A) which is slight relative to the overall shape.

FIG. 1C To compute the best possible performance the ophthalmologist interactively uses the methods and instruments to direct shape information and laser beam for multizone ablation (44) to the patients cornea (4). The laser (41) beam (44) are directed to ablate the surface of the Corneal Ablation Area (18), create a changed curvature of the surface in the corneal ablation area (18), a new changed slope and curvature as a result of the non ablated meniscus +2 Diopter and above effect (5) in the lower quadrant of the optical zone (19) and new relationship between the slope angle created by the Meniscus blending contours phased to laser beam size to blend into the surface of the corneal ablated area (18). Identified are predetermined Meniscus blending contours phased to the beam size (5A). Identified are the interactive control paths carrying bi-directional information from the patients cornea (4) to the ophthalmologist (32), the centration and ablation management (31), computer (25), and laser (41) and laser beam for multizone ablation (44). Also identified is the preserved Lamellar Pediculated disk with epithelium, Bowman and Stroma (16). At the completion of ablation sequence, the patient's retained epithelium is replaced on the central and paracentral area.

FIG. 1D Shows the eye corrected for presbyopia and the accurate changed shape of the cornea to determined visual acuity. The optical, anatomical, and physiological data are shown as the non-ablated peripheric cornea (15B) returned under the flap, a corrected meniscus with +2 diopter and above correction under the flap, the (5B) meniscus blending contours phased to a laser beam size under the flap and the Corneal Ablation area now under the flap (18). The flap being (16A) the Lamellar Pediculated Corneal Disk with Epithelium, Bowman and Stroma is returned over the cornea to complete the correction for presbyopia. With this method of accurate corneal shape topography presbyopia is precisely corrected and designed with the individual's cornea in mind.

FIG. 2E According to principles of optics, where curvature and slope of the cornea in a meridional plane containing the reference axis of the measurement system, which is normal to the cornea, instantaneous power is defined as: $Pi=(n-1)/ri$ (1) larger diameter ablations produce less variations in the refractive power of the cornea. When the surgeon considers relatively large ablation area as 7.5 m.m diameter ablation produces slight modification in corneal power. The small width of the non ablated "Bean/Kidney shaped area" (5& 5A) just a small height will produce some diopters of increased power curvature. In this manner the surgeon creates an area of "plus effect" FIG. 2E (5 and 5A) without disturbing or even correcting existing ammetropias, adding the advantage of correction of near distance for presbyopia patients. The videokerotograph 29, which is a device used to extract shape information from the patient's cornea, passes Topographic data from the Cornea (4) and Miniscus Blending Topographic Data (5A) to the microcomputer (25) and image processor (25A). (5 and 5A) Non-Ablated Miniscus Contoured under Flap with +2 Diopter and above effect is shown as a lateral cross-section indicating the new curvature, (18) is the Corneal Ablated Area and (15) is the Non-Ablated Peripheric Cornea with corrected presbyopia will be detected by the videokerotograph 29.

In order achieve a proper centration and for placement of relatively small "Bean/Kidney shaped area" (5 & 5A) the eye may be immobilized. If placement of relatively small "Bean/Kidney shaped area" is to achieved by placing non-ablatable or ablative mask the eye may be immobilized. Proper centration (32) also using centration, pupil placement magnification (31) and other surgeon's magnification and alignment instrument (30) can be performed by tracking mechanism or immobilization or indenting marks, Projection of Dilated Pupilary Border (17).

Computational methods and laser control is used to create the accurate "Bean/Kidney shaped area" (5&5A) with resulting correction of presbyopia.

Preferred Embodiment—Operation

The proper method and innovative technique to correct presbyopia is to determine the change in the shape of the cornea ( ) of the eye using a "protected kidney shaped area oriented nasally" (5&5A). Using available refractive surgical tools usually found in the 193 nanometers wavelengths (41 & 44) to ablate tissue, a planned topography changes the shape of the cornea to correct presbyopia.

FIGS. 1–1D and FIGS. 2–2D show the progression of the technique and Computational methods and laser control is used to create the accurate "Bean/Kidney shaped area" (5&5A) with resulting correction of presbyopia. "Bean/Kidney shaped area" (5&5A) is placed and contoured in the lower quadrant of the central optical zone (19) and new relationship between the slope angle created by the Meniscus blending contours phased to laser beam size to blend into surface corneal ablated area (18). Proper centration (32 the centration, pupil placement magnification (31) and other surgeon's magnification and alignment instrument (30) by tracking mechanism or immobilization or indenting marks, Projection of Dilated Pupilary Border (17) the surgeon aligns the cornea (4) and centers the cornea (4) along the optical axis of the eye and "Bean/Kidney shaped area" (5&5A) is planned then placed and contoured in the lower quadrant of the central optical zone (19).

FIGS. 1–1D and FIGS. 2–2D show the progression of the technique to accurately change the shape of the cornea (4) to achieve a visual acuity for patients with presbyopia. A area of Non-Ablated Peripheric Cornea (15) is identified and marked at is the region of the cornea in the operation will be carried out. A Lamellar Pediculated corneal disk with Corneal Epithelium (approx. 40–50 microns thick), Bowman's Membrane and Stroma (consisting of multiple layers of collagen fibers, kerotocytes and water) (16) is then marked is delineated, mechanically using a dulled Beaver Blade or by laser beam or a microkerotome and left attached and preserved for replacement. The removal of the Lamellar Pediculated corneal disk with Corneal Epithelium (approx. 40–50 microns thick), Bowman's Membrane and Stroma (consisting of multiple layers of collagen fibers, kerotocytes and water) (16) produces and exposed area on the cornea (4) a corneal area of stromal lamellae, kerotocytes Descemet's membrane and Endothelial cells. After ensuring even hydration and smooth Lamellar Pediculated corneal disk with Corneal Epithelium (approx. 40–50 microns thick), Bowman's Membrane and Stroma (consisting of multiple layers of collagen fibers, kerotocytes and water) (16) removal, the surgeon verifies smooth and complete removal. This relatively large exposed stromal area is large enough to be ablated without producing any major change in refractive power of the cornea. The technique will leave a protected area in the interior half of the cornea that is not to ablated as defined "Bean/Kidney shaped area" (5 & 5A) while modifying the remaining dimensional optical characteristics of the cornea are illustrated in FIGS. 1–1D and FIGS. 2–2E.

Using the instruments described in FIGS. 1–1D and 2–2E the patient actively fixates on the scene of fixation and the pupil is centered under the reticule that is visible to the surgeon through one piece of the binocular microscope. Treatment is commenced at the time of optimal corneal hydration. The patient is requested to maintain fixation on the scene of fixation and report any deviation even though advanced tracking and computation systems will compensate and align of deviation in real time.

The transition form the corneal ablation area (18) and Non-Ablated Peripheric Cornea (15) should be smooth in order to avoid symptoms and proliferation or scar tissue. Improved scanning and corneal topography have opened the way for the precisely designed transition although ablative masks with beveled periphery may be used to achieve the smooth transition. Once the corneal ablation area (18) has been treated and blended with Non-Ablated Peripheric Cornea (15) the definition and markers defining the protected "Bean/Kidney shaped area" (5 & 5A) will emerge with its characteristic change of slope and angle and shape.

The transition of the "Bean/Kidney shaped area" to the corneal ablation area (18) is computed and it dependent on the correction required and phased matched to the beam size of the radiation equipment being used. To assist the surgeon to place and contour this complex corneal topography of "Bean/Kidney shaped area" (5 & 5A) to smoothly change the shape of the cornea to achieve visual acuity to correct presbyopia computational and image processing image (25A) and Microcomputer (25) workstations with laser beam control systems controlled to compute the best possible performance the ophthalmologist interactively uses the methods and instruments to direct shape information and laser beam for multizone ablation (44) to the patients cornea (4). The laser (41) beam (44) are directed to ablate the surface of the Corneal Ablation Area (18), create a changed curvature of the surface in the corneal ablation area (18), a new changed slope and curvature as a result of the non ablated meniscus +2 Diopter and above effect (5).

Upon finishing the proper ablation the Lamellar Pediculated corneal disk with Corneal Epithelium (approx. 40–50 microns thick), Bowman's Membrane and Stroma (consisting of multiple layers of collagen fibers, kerotocytes and water) (16) is returned and is repositioned to the original position and the surgery is complete.

CONCLUSIONS RAMIFICATIONS AND SCOPE

The method innovation and surgery will have ramifications on the characterization of the elastic properties and the age related biochemical and accommodation, the mechanism by which the human eye focus on near objects.

Further the operation may have ramifications on the biophysical/biochemical standpoint on alpha-crystalline aggregation into the protein equivalent of micelles.

Further the technique will have ramification on the measurements of the eyes and its components in the average quadrant analyses, refractive, oblique, lateral and Negative lateral, average surface roughness and average slope and geometric ratios such as symmetry.

Also the technique and invention will have ramifications on corneal lens design and implanted ocular lens designed along the parameters set forth in this invention in order to correct presbyopia.

The technique and invention will have ramifications on devices used to extract shape information from the patient's cornea. Such that when the shape extracting devices bounce light rays bounce of the front of the cornea simulations for the correction of presbyopia and then the historical measurements of the patient's eye are possible. The system so described and illustrated in the invention has the capability to save the information into a file.

The invention will have ramification on the Sphere/Cylinder Visualization.

This invention will ramification in the computer aided corneal lens design and the interactive visualization of the results.

The invention will have research implication in field of human visual performance.

The invention will have ramification in Ophthalmic Optics and will have ramifications on the distance from the posterior nodal to the retina which will increase and decline with eccentricity.

The invention will have ramification in spatial modulation transfer in the stereoscopic threshold of the human eyes.

The invention will have ramification in Optical power visualization (in Diopters).

The invention will have ramification in interpretation of presbyopia corrected eyes when viewed as topographical data in the "absolute", "normalized" "Isometric" and "deferential" scales.

The invention will have ramification in hydration between the Aqueous Humor of the Anterior Chamber, Enothelium (post corneal epithelium) Decemet's membrane, Substantia Propria, Bowwman's membrane and the anterior Corneal Epithelium.

The invention will have ramification in the field of mathematics and application of conformal mapping and its application to the correction of presbyopia.

The invention will have ramification in the modeling the cornea.

The invention will have ramification in fluid transportation mechanism in the eye.

The invention will have ramification in Optic flow and the perception of self-motion The invention will have ramification in visual science field.

This innovative technique will correct presbyopia in a reasonably predictable way. after measuring the shape of the cornea in patient with presbyopia the invention will correct the presbyopia by adding an important feature to the sub surface of the cornea to a determined visual acuity.

The description of the invention, method and technique have advantages over current approaches: it is more accurate, it directly recovers position of the cornea, it produces a continuos map over the entire surface, it prevents over correction and the practitioner can see important new features and the invention opens the way to develop more complex shapes precisely designed with individual's cornea in mind.

What is claimed is:

1. A method of correcting presbyopia in a human eye comprising:

applying fixation means to fixate an eye;

applying an ablation mask to at least a portion of a corneal surface of the eye;

ablating non-masked portions of the corneal surface of the eye so as to define a protected, non-ablated area having a kidney bean shape oriented nasally, the non-ablated area having gradient blending with the corneal surface and an optical effect of +2 diopters or greater;

measuring the geometrical characteristics of the resulting corneal surface.

2. A method of correcting presbyopia in a human eye comprising:

measuring geometrical characteristics of a corneal surface of the eye;

applying a fixation means to fixate an eye;

ablating portions of the corneal surface of the eye so as to define a protected, non-ablated area having a kidney bean shape oriented nasally, the non-ablated area having gradient blending with the corneal surface and an optical effect of +2 diopters or greater;

measuring the geometrical characteristics of the resulting corneal surface after ablation.

* * * * *